(12) United States Patent
Margolis et al.

(10) Patent No.: US 7,968,298 B2
(45) Date of Patent: Jun. 28, 2011

(54) USE OF HERPESVIRUSES, HERPESVIRUS PROTEINS AND NUCLEIC ACIDS ENCODING THE PROTEINS TO INHIBIT CCR5-TROPIC HIV-1 INFECTION AND REPLICATION

(75) Inventors: Leonid B. Margolis, Kensington, MD (US); Jean-Charles Grivel, Frederick, MD (US); Paolo Lusso, Milan (IT)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1479 days.

(21) Appl. No.: 10/473,560

(22) PCT Filed: Mar. 28, 2002

(86) PCT No.: PCT/US02/10048
§ 371 (c)(1),
(2), (4) Date: Mar. 5, 2004

(87) PCT Pub. No.: WO02/078740
PCT Pub. Date: Oct. 10, 2002

(65) Prior Publication Data
US 2005/0123510 A1    Jun. 9, 2005

Related U.S. Application Data

(60) Provisional application No. 60/279,568, filed on Mar. 28, 2001.

(51) Int. Cl.
*C12Q 1/70* (2006.01)
*G01N 33/53* (2006.01)
(52) U.S. Cl. ............................. 435/7.1; 435/5
(58) Field of Classification Search ........................ None
See application file for complete search history.

(56) References Cited

FOREIGN PATENT DOCUMENTS
WO    WO 98/04286    *    2/1998

OTHER PUBLICATIONS

Berger EA et al "Chemokine receptors as HIV-1 coreceptors: roles in viral entry, tropism, and disease". Annu Rev Immunol. 1999;17:657-700.*
Mosier DE et al. "Highly potent RANTES analogues either prevent CCR5-using human immunodeficiency virus type 1 infection in vivo or rapidly select for CXCR4-using variants". J Virol. May 1999;73(5):3544-50.*
Lusso, P. and Robert Gallo "Human herpesvirus 6 in AIDS" Immunology Today 16:67-71 (1995).*
Losso P et al. "Human herpesvirus 6A accelerates AIDS progression in macaques" Proc Natl Acad Sci U S A. Mar. 20, 2007;104(12):5067-72. Epub Mar. 14, 2007.*
Clark DA "Human herpesvirus 6" Rev Med Virol. May-Jun. 2000;10(3):155-73.*

* cited by examiner

*Primary Examiner* — Bo Peng
(74) *Attorney, Agent, or Firm* — Kilpatrick Townsend & Stockton LLP (57) ABSTRACT

It has been discovered that herpesviruses can trigger an increase in the production of HIV-suppressive chemokines, and that these chemokines block the CCR5 receptor, which is used as a co-receptor with CD4 in the CCR5-tropic forms of HIV-1 that predominate in early stage HIV-1 infection. Use of live, attenuated or killed herpesviruses, or of herpesvirus proteins which trigger an increase in production of HIV-suppressive chemokines, or of nucleic acids encoding those proteins, can likewise be used to prevent establishment of HIV-1 infection or to inhibit HIV-1 replication. The invention provides uses, methods and compositions related to these discoveries.

4 Claims, 3 Drawing Sheets

SEQUENCE LISTING

```
<160> NUMBER OF SEQ ID NOS: 7

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence:SF162
      forward primer

<400> SEQUENCE: 1
tatgcaacag gagacataat aggagatata ag                                     32

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:SF162
      reverse primer

<400> SEQUENCE: 2
tagttccatt agtgttattt ggccctatag                                        30

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:LAV.04
      forward primer

<400> SEQUENCE: 3
gttacaatag gaaaaatagg aaatatgaga ca                                     32
```

```
<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:LAV.04
      reverse primer

<400> SEQUENCE: 4
tcacttcctt cagtgttatt tgacccttc                                      29

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:primer
      derived from open reading frame U67 conserved in subgroups
      A and B of HHV-6

<400> SEQUENCE: 5
caaagccaaa ttatccagag cg                                             22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:primer
      derived from open reading frame U67 conserved in subgroups
      A and B of HHV-6

<400> SEQUENCE: 6
cgctaggttg aggatgatcg a                                              21

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:probe
      derived from open reading frame U67 conserved in subgroups
      A and B of HHV-6

<400> SEQUENCE: 7
caccagacgt cacacccgaa ggaat                                          25
```

USE OF HERPESVIRUSES, HERPESVIRUS PROTEINS AND NUCLEIC ACIDS ENCODING THE PROTEINS TO INHIBIT CCR5-TROPIC HIV-1 INFECTION AND REPLICATION

CROSS-REFERENCES TO RELATED APPLICATIONS

This application claims the benefit of U.S. Provisional Application No. 60/279,568, filed Mar. 28, 2001, the contents of which are incorporated by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

This invention relates to the prevention of establishment of infection by HIV-1, or delaying or inhibiting the progression to AIDS in patients infected with CCR5-tropic HIV-1.

BACKGROUND OF THE INVENTION

HIV-1 infects target cells via a receptor complex formed by CD4 and a chemokine receptor, primarily CCR5 or CXCR4 (Berger, E. et al., *Ann. Rev. Immunol.* 17:657-700 (1999)). Commonly, HIV-1 transmission is mediated by CCR5-tropic variants, also designated slow/low, non-syncytia-inducer, or macrophage-tropic, which dominate the early stages of HIV-1 infection and frequently persist during the entire course of the disease (Fenyo, E. M. et al. *J. Virol.* 62:4414-9 (1988); Tersmette, M. et al. *Lancet* 1:983-5 (1989); Schuitemaker, H. et al. *J. Virol.* 66:1354-60 (1992); Fenyo, E. M. *AIDS* 7:1673-4 (1993); Koot, M. et al. *Ann. Intern. Med.* 118:681-688 (1993); Bjorndal, A. et al. *J. Virol.* 71:7478-87 (1997); Scarlatti, G. et al. *Nature Med.* 3:1259-65 (1997); Connor, R. I. et al., *J. Exp. Med.* 185:621-8 (1997)). In contrast, HIV-1 variants that use CXCR4 are typically detected at the later stages, and are associated with a rapid decline in CD4 T cells and progression to AIDS (Fenyo, E. M. et al., 1988, supra; Bjorndal, A. et al. *J. Virol.* 71:7478-87 (1997); Scarlatti, G. et al., 1997, supra; Connor, R. I. et al., 1997, supra; Fouchier, R. A. et al., *Virology* 219:87-95 (1996); Koot, M. et al. *J. Infect. Dis.* 179:254-8 (1999)). Disease progression is also associated with the emergence of concurrent infections that may affect the course of HIV disease by mechanisms that remain unknown.

Human herpesvirus 6 (HHV-6) is a double-stranded DNA virus originally isolated from immunocompromised patients with different lymphoproliferative disorders and described as a B-lymphotropic virus (Salahuddin, S. Z. et al., *Science* 234:596-601 (1986)). Shortly thereafter, however, a primary tropism for CD4+ T lymphocytes was documented both in vitro (Lusso, P. et al., *J. Exp. Med.* 167:1659-1670 (1988)) and in vivo (Takahashi, K. et al., *J. Virol.* 63:3161-3163 (1989)). Two major viral subgroups, designated A and B, have been defined, which form two segregated clusters with unique genetic, biologic and immunologic characteristics (Lusso, P. *Antiviral Research,* 31:1-21 (1996)). While HHV-6 B is highly prevalent in the human population in all geographic areas (Lusso, P. *Antiviral Research,* 31:1-21 (1996)), the epidemiology of HHV-6 A is still largely undefined. Primary infection with HHV-6 B, which occurs almost universally during early childhood, has been linked to the etiology of exanthema subitum, a usually benign febrile disease (Yamanishi, K. et al., *Lancet i,* 1065 (1988)). Conversely, little is known about the time and pathologic consequences of primary HHV-6 A infection.

In the adult, HHV-6 infection and/or reactivation have been associated with a wide variety of diseases, although most of these associations have not been substantiated by rigorous epidemiological and virological studies. Considerable interest was raised by recent data on a possible link between HHV-6 and multiple sclerosis (Challoner, P. B. et al., *Proc. Natl. Acad. Sci. USA* 92:7440-4 (1995)), but the evidence hitherto accumulated is controversial (Soldan, S. S. et al., *Nat. Med.* 3:1394-7 (1997); Martin C et al. *Acta Neurol Scand;* 95:280-283 (1997)). In immunocompromised people, HHV-6 acts as an opportunistic agent that may cause life-threatening infections of the respiratory tract and the central nervous system, as well as bone marrow and organ graft failure (Lusso, P. *Antiviral Research*, supra).

Several lines of evidence have led to speculation that HHV-6 may act as an immunosuppressive agent in vivo. Both HHV-6 subgroups induce severe thymocyte depletion in heterochimeric SCID hu thy/liv mice, showing a predominant tropism and cytopathicity for immature thymic precursor cells (Gobbi, A. et al., *Journal of Experimental Medicine,* 189:1953-1960 (1999)). Disseminated HHV-6 A and B coinfection has been linked with a progressive and ultimately fatal immunodeficiency syndrome in an HIV-negative child (Knox, K. K. et al., *Clin. Infect. Dis.* 20:406-13 (1995)). Moreover, active HHV-6 infection, as revealed by the detection of plasma viremia, was associated with lymphocytopenia and with defective lymphocyte proliferation to recall antigens in patients who received allogeneic stem cell transplantation. Consistent with these observations, it has been suggested that HHV-6, particularly subgroup A, may act as a cofactor in the progression of human immunodeficiency virus (HIV) disease, which might contribute, either directly or indirectly, to the depletion of $CD4^+$ T cells and the other dysfunctions of the immune system associated with full-blown AIDS (Lusso, P. et al., *Immunology Today* 16:67-71 (1995)). It has also been suggested that HHV-6 down-regulates the CXCR4 receptor, making CD4+ lymphocytes resistant to T lymphocyte-tropic HIV-1 strains. (Yasukawa et al., J. Immunol. 162:5417-5422 (1999). Progress in this area of investigation has been hampered by the lack of reliable and easily accessible study models.

BRIEF SUMMARY OF THE INVENTION

The invention provides uses, methods and compositions useful to prevent establishment of HIV-1 infection or, in an individual already infected with HIV-1, to delay or to inhibit progression of CCR5-tropic HIV infection to CXCR4-tropic infection, which is associated with rapid declines in T-cell counts and progression to AIDS.

Specifically, the invention provides the use of attenuated herpesviruses which increase production in lymphoid tissue of one or more chemokines selected from the group consisting of RANTES, MIP-1α, or MIP-1β, for the manufacture of a medicament to inhibit infection by or replication of CCR5-tropic HIV-1. In preferred forms, the herpesvirus is selected from the group consisting of human herpesvirus ("HHV")-

6A, HHV-6B, and HHV-7. In particularly preferred embodiments, the HHV-6 is HHV-6A. The chemokine can be RANTES, MIP-1α, or MIP-1β, or a combination of these. In preferred forms, the chemokine is RANTES or MIP-1β.

In another group of embodiments, the invention provides for the use of a isolated protein from a herpesvirus, which protein alone or in combination with other herpesvirus proteins, increases production in lymphoid tissue of one or more chemokines selected from the group consisting of RANTES, MIP-1α, or MIP-1β, for the manufacture of a medicament to inhibit growth or replication of CCR5-tropic HIV-1. In preferred forms, the herpesvirus is selected from the group consisting of human herpesvirus ("HHV")-6A, HHV-6B, and HHV-7. In particularly preferred embodiments, the HHV-6 is HHV-6A. The chemokine can be ANTES, MIP-1α, or MIP-1β, or a combination of these. In preferred forms, the chemokine is RANTES or MIP-1β.

The invention further provides the use of an isolated nucleic acid encoding a protein from a herpesvirus, which protein increases production in lymphoid tissue of one or more chemokines selected from the group consisting of RANTES, MIP-1α, or MIP-1β, for the manufacture of a medicament to inhibit growth or replication of CCR5-tropic HIV-1. In preferred forms, the herpesvirus is selected from the group consisting of human herpesvirus ("HHV")-6A, HHV-6B, and HHV-7. In particularly preferred embodiments, the HHV-6 is HHV-6A. The chemokine can be RANTES, MIP-1α, or MIP-1β, or a combination of these. In preferred forms, the chemokine is RANTES or MIP-1β.

In yet another set of embodiments, the invention provides the use of a lymphoid tissue-tropic herpesvirus which increases production in lymphoid tissue of one or more chemokines selected from the group consisting of RANTES, MIP-1α, or MIP-1β, for the manufacture of a medicament to inhibit growth or replication of CCR5-tropic HIV-1. In preferred forms, the herpesvirus is selected from the group consisting of human herpesvirus ("HHV")-6A, HHV-6B, and HHV-7. In particularly preferred embodiments, the HHV-6 is HHV-6A. The chemokine can be RANTES, MIP-1α, or MIP-1β, or a combination of these. In preferred forms, the chemokine is RANTES or MIP-1β.

Further, the invention provides the use of a killed herpesvirus, which killed herpesvirus increases production in lymphoid tissue of one or more chemokines selected from the group consisting of RANTES, MIP-1α, or MIP-1β, for the manufacture of a medicament to inhibit growth or replication of CCR5-tropic HIV-1. 17. In preferred forms, the herpesvirus is lymphoid tissue-tropic. In preferred forms, the herpesvirus is selected from the group consisting of human herpesvirus ("HHV")-6A, HHV-6B, and HHV-7. In particularly preferred embodiments, the HHV-6 is HHV-6A. The chemokine can be RANTES, MIP-1α, or MIP-1β, or a combination of these. In preferred forms, the chemokine is RANTES or MIP-1β.

In another important group of embodiments, the invention provides methods of inhibiting growth or replication of CCR5-tropic HIV-1. The methods comprise administering an agent selected from the group consisting of: an attenuated herpesvirus which increases production in lymphoid tissue of one or more chemokines selected from the group consisting of RANTES, MIP-1α, or MIP-1β, a protein from a lymphoid tissue-tropic virus, which protein increases production in lymphoid tissue of one or more chemokines selected from the group consisting of RANTES, MIP-1α, or MIP-1β, a nucleic acid encoding a protein from a lymphotropic virus, which protein increases production in lymphoid tissue of one or more chemokines selected from the group consisting of RANTES, MIP-1α, or MIP-1β, and a killed or living lymphotropic herpesvirus which killed or living virus increases production in lymphoid tissue of one or more chemokines selected from the group consisting of RANTES, MIP-1α, or MIP-1β. 20. In preferred forms, the agent is an attenuated lymphoid tissue-tropic herpesvirus which increases production in lymphoid tissue of one or more chemokines selected from the group consisting of RANTES, MIP-1α, or MIP-1β. In especially preferred forms, the herpesvirus is selected from the group consisting of human herpesvirus ("HHV")-6A, HHV-6B, and HHV-7 and in the most preferred embodiment is HHV-6A.

In yet another important group of embodiments, the invention provides compositions comprising an agent selected from the group consisting of: an attenuated herpesvirus which increases production in lymphoid tissue of one or more chemokines selected from the group consisting of RANTES, MIP-1α, or MIP-1β, a protein from a herpesvirus, which protein increases production in lymphoid tissue of one or more chemokines selected from the group consisting of RANTES, MIP-1α, or MIP-1β, a nucleic acid encoding a protein from a herpesvirus, which protein increases production in lymphoid tissue of one or more chemokines selected from the group consisting of RANTES, MIP-1α, or MIP-1β, and a lymphoid tissue-tropic herpesvirus which increases production in lymphoid tissue of one or more chemokines selected from the group consisting of RANTES, MIP-1α, or MIP-1β, in a pharmaceutically acceptable carrier. In one set of preferred embodiments, the agent in the composition is an attenuated lymphoid tissue-tropic herpesvirus which increases production in lymphoid tissue of one or more chemokines selected from the group consisting of RANTES, MIP-1α, or MIP-1β. In particularly preferred embodiments, the herpesvirus is selected from the group consisting of human herpesvirus ("HHV")-6A, HHV-6B, and HHV-7, with HHV-6A being the most preferred. In some preferred embodiments, the agent comprises one or more proteins from a herpesvirus, which agent increases production in lymphoid tissue of one or more chemokines selected from the group consisting of RANTES, MIP-1α, or MIP-1β. In some other preferred embodiments, the agent in the composition is a nucleic acid encoding one or more proteins from a herpesvirus, which protein increases or proteins increase production in lymphoid tissue of one or more chemokines selected from the group consisting of RANTES, MIP-1α, or MIP-1β. Finally, in some preferred embodiments, the agent in the composition is a killed or living lymphoid tissue-tropic herpesvirus, which killed or living herpesvirus increases production in lymphoid tissue of one or more chemokines selected from the group consisting of RANTES, MIP-1α, or MIP-1β.

BRIEF DESCRIPTION OF THE DRAWINGS

FIG. 1a. Kinetics of HIV-1 replication of CCR5- and CXCR4-tropic variants in tissues coinfected with HHV-6. Each point represents the mean of 54 pooled tissue blocks from a single donor infected with CCR5-tropic variant, SF162 alone (open boxes), CXCR4-tropic variant LAV.04 alone (Δ) or coinfected with HHV-6 (SF162: filled boxes; LAV.04: filled triangles). FIG. 1b. Average change in CCR5- and CXCR4-tropic HIV-1 replication in HHV-6-coinfected tissues from different donors (n=17 for the CXCR4-tropic variant LAV.04 and n=10 for the CCR5-tropic variant SF162), relative to matched tissues infected with the corresponding HIV-1 variant alone. Mean+ S.E.M. of data obtained in experiments with 54 pooled matched tissue blocks from each donor. FIG. 1c. Average change in HIV-1 replication in HHV-6-infected human lymphoid tissues coinfected with a mixture of CCR5-tropic HIV-1 variant SF162 and CXCR4-tropic variant LAV.04. Replication of each HIV variant in HHV-6 infected tissue is expressed relative to that in matched tissues infected with the HIV-1 variant mixture only. Variant-specific real-time RT PCR analysis of RNA extracted from the culture medium. Mean+S.E.M. of data obtained in experiments with 54 pooled matched tissue blocks from each of five donors. FIG. 1d. Average change in replication of two dual-tropic HIV-1 variants, 89.6 and 89-v345.SF in HHV-6 coinfected tissues from two different donors relative to matched tissues infected with the corresponding HIV-1 variant alone. Mean+S.E.M. of data obtained in experiments with 54 pooled matched tissue blocks from each donor.

FIG. 2a. Kinetics of RANTES production in a representative experiment. Each point represents the mean of 54 pooled tissue blocks from the same donor as in FIG. 1a. Blocks were either uninfected (open circles), or infected with HHV-6 (filled circles), SF162 (open boxes), LAV.04 (open triangles), or coinfected with HHV-6 and SF162 (filled boxes) or with HHV-6 and LAV.04 (filled triangles). FIG. 2b. Average change in RANTES production in human lymphoid tissues infected ex vivo with either HHV-6 alone, HIV-1 alone, or a mixture of these two viruses. Each bar represents the mean+S.E.M of RANTES production in 54 pooled blocks from each of 10-34 donors, relative to matched uninfected tissues.

DETAILED DESCRIPTION

Introduction

Surprisingly, it has been discovered that it is possible to use certain viruses that upregulate chemokines to prevent entry of CCR-tropic HIV-1 into a cell, or to delay or to inhibit the replication of HIV-1 in the body during early stages of infection. The discovery provides new methods and compositions to block infection by HIV-1, and to ameliorate or to treat HIV infection in persons who have not yet progressed to the severe immunosuppression and AIDS that characterizes the CXCR4-tropic forms of HIV infection.

It has now been discovered that viruses, and in particular, certain herpesviruses, upregulate HIV-1 suppressive chemokines. It has been known since 1995 that the chemokines RANTES, MIP-1α, and MIP-1β, are HIV-suppressive factors produced by CD8+ T cells. Cocchi et al., Science 270:1811-1815 (1995). But exploitation of this finding has been difficult since systemic administration of chemokines tends to have undesirable side effects and since it may not be possible to administer systemically dosages that result in concentrations sufficiently high in the lymphoid tissue in which HIV resides to suppress replication of the virus. Surprisingly, it has been discovered that these problems can be solved by the use of herpesviruses, which result in the upregulation of HIV-1 suppressive chemokines in the very tissues in which HIV tends to reside, resulting in a high localized concentration.

It has also now been discovered that these HIV-suppressive chemokines bind to the CCR5 receptor ("R5"). The variants of HIV-1 that predominate in early stages of HIV-1 infection use R5 along with CD4 as co-receptors for cell entry and infection. Variants that predominate in later stages of HIV-1 infection, characterized by rapid T cell depletion and progression to AIDS, instead use CXCR4 as a co-receptor with CD4. Thus, by blocking the co-receptor necessary for cell entry in early stage HIV-1 infection, the methods and compositions of the invention can reduce the ability of the virus to enter cells in persons not yet infected with HIV, or to replicate in HIV-1 infected patients who have not yet progressed to AIDS. The methods and compositions of the invention are therefore useful by themselves to reduce overall viral load.

The methods and compositions of the invention can also be used in conjunction with standard therapies, such as protease inhibitors, nucleoside analogs, or the combinations of these agents known as Highly Active Anti-Retroviral Therapy (HAART), to delay progression to the severe immunosuppression that characterizes later stage HIV disease. Such delays are highly useful since health care costs and, of course, risk to the patient increase dramatically as HIV disease progresses into AIDS. Moreover, by blocking receptors necessary for cell entry and infection by HIV, the methods and compositions of the invention can be administered to persons in high risk populations to reduce the chance that HIV infection will be established upon exposure. Further, the methods and compositions of the invention can be used to reduce the possibility of establishment of HIV infection in individuals who may have been exposed to HIV. For example, health care workers who have had a "needle stick" or individuals who have engaged recently in unprotected sex can use the methods and compositions of the invention to reduce the likelihood of establishment of HIV infection in their bodies.

Cytokine Modulation

Pathogen invasion triggers immune effector mechanisms that are coordinated by a complex network of cytokines, particularly chemokines. Paradoxically, some microbes have learned how to benefit from cytokine- and chemokine-mediated immune reactions by either exploiting them (e.g., replication of certain strains of HIV is enhanced in the presence of specific chemokines (Schmidtmayerova, H. et al., Nature 382:767 (1996); Kinter, A. et al. Proc. Natl. Acad. Sci. USA 95 (20):11880-11885 (1998); Margolis, L. B. et al. J. Clin. Invest. 101 (9):1876-1880 (1998)) or subverting them (e.g., human cytomegalovirus encodes a chemokine receptor that scavenges the chemokine RANTES (Bodaghi, B. et al. J. Exp. Med. 188 (5):855-866 (1998)). Such strategies allow microbes to create conditions favorable for their own maintenance (Murphy, P. M. Nature Immunol. 2 (2):116-122 (2001)). See also, Vilcek and Sen in Fields et al., eds., *Fields Virology*, Lippincott Williams and Wilkins, Philadelphia Pa. (3rd Ed., 1996) (hereafter, "*Fields Virology*"); Knipe and Howley et al., eds. *Fields Virology*, Lippincott Williams and Wilkins, Philadelphia Pa. (4th ed., 2001). Various microbes, however, have different chemokine/chemokine receptor requirements for their optimal maintenance, and what is optimal for one microbe may be detrimental for another.

For example, in mice lymphocytic choriomeningitis virus infection abolishes replication of hepatitis B virus, and this process is mediated by TNF-alpha and IFN-gamma (Guidotti, L. G. et al. Proc. Natl. Acad. Sci. USA 93 (10):4589-4594 (1996)). In vitro, cell infection with HTLV-1 (Moriuchi, H. et al. J. Exp. Med. 187 (10):1689-1697 (1998)) or with HTLV-II (Casoli, C. et al. Blood 95 (9):2760-2769 (2000)) inhibits replication of HIV-1 variants that use CCR5 coreceptor for infection. This process is mediated by upregulation of CC chemokines (Cocchi, F. et al. Science 270 (5243):1811-1815 (1995)) for which CCR5 is a natural receptor (Combadiere, C. et al. J. Leukoc. Biol. 60 (1):147-152 (1996); Samson, M. et al. Biochemistry 35 (11):3362-3367 (1996)).

The present invention exploits the realization that the immunomodulatory effects of one microorganism can protect against a threat posed by a second microorganism. Use of microorganisms that upregulate chemokines that block the CCR5 receptor can protect CCR5 receptor-bearing cells from infection by CCR5 tropic variants of HIV. As noted above, early stages of HIV infection are characterized by a predominance of variants of HIV-1 which use CCR5 as a co-receptor with CD4 for binding to cells ("CCR5-tropic" or "R5 tropic" forms of HIV). Thus, administration of viruses that can increase the presence of CCR5-binding chemokines (or of agents derived from those viruses) can prevent the infection of CCR5-bearing cells by R5-tropic forms of HIV, possibly reducing the possibility that an HIV infection will be established. Accordingly, the compositions of the invention can be administered to persons at risk for acquiring HIV-1 infection (for example, the compositions can be administered to hospital workers who have received a "needle stick" or to persons who have engaged in unprotected sex).

In persons with an established HIV infection, the administration of viruses that can increase the presence of CCR5-binding chemokines (or of agents derived from those viruses) reduces overall viral load, giving other antiviral therapy an increased opportunity to work, and delaying progression to AIDS. Accordingly, the compositions of the invention can be administered to persons who have already become infected by HIV-1, but have not yet progressed to AIDS. Conveniently, this can be determined by T-cell counts, which provide a general measure of the status of the immune system of an HIV-positive individual. Normal T-cell counts and of declines indicative of progression to AIDS are well known in the art.

In preferred embodiments, the HIV-suppressive chemokines are RANTES, MIP-1α, and MIP-1β. These chemokines are known to be HIV-suppressive. See, Cocchi et al., supra. In especially preferred embodiments, the chemokine is RANTES or MIP-1β, or both.

Viruses Suitable for Use in the Methods and Compositions of the Invention

Viruses preferred in the methods and uses of the invention are herpesviruses. Based on the similarity of herpesvirus proteins and epidemiology, it is expected that other herpesviruses will have the effect of triggering increased production of the HIV-suppressive chemokines RANTES, MIP-1α, and MIP-1β in lymphoid tissue.

Herpesviruses are classified as alpha, beta, or gamma herpesviruses; for purposes of the invention, however, members of all the classes can be used. Herpesviruses suitable in the methods, uses and compositions of the invention include human herpesvirus ("HHV") 6A, HHV-6B, HHV-7, HHV-8, Epstein-Barr virus ("EBV"), cytomegalovirus ("CMV"), herpes simplex virus ("HSV")-1 and HSV-2, and varicella-zoster virus. In preferred embodiments, the herpesvirus is lymphoid tissue-tropic. In more preferred embodiments, the herpesvirus is not known to have any, or at least with any significant, pathogenicity in humans. In particularly preferred forms, the herpesviruses are human herpesvirus ("HHV")-6 and HHV-7. There are two variants of HHV-6, A and B. HHV-6B is associated with a febrile infection, exanthum subitum ("ES"), that affects young children; a majority of the population is infected with HHV-6B in childhood. HHV-6A has not been established to be associated with any disease in humans. While either form of HHV-6 can be used in the compositions, uses, and methods of the invention, HHV-6A is generally preferred since it is not known to be associated with any disease. If desired, HHV-6B can be used since most individuals in the population have been infected with HHV-6B in infancy, have previously contracted ES, and can be presumed to be able to contain the infection without significant pathology. HHV-6 is thought to be spread by saliva, and HHV-6 virus is found in the saliva in considerable amounts. Thus, HHV-6A or B are especially preferred because they can be administered in a simple mouth rinse or wash. Conveniently, the mouth rinse can have a composition with a pH and salt content similar to that of saliva.

The virus used can be wild-type or attenuated. If the virus to be used is not attenuated, it is preferred that the virus is lymphoid tissue-tropic and, in even more preferred embodiments, is not a known pathogen. Tissue tropisms of the various herpesviruses are known in the art. See, e.g., Knipe and Howley et al., eds. *Fields Virology*, Lippincott Williams and Wilkins, Philadelphia Pa. ($4^{th}$ Ed., 2001). HHV-6B can be used. Although HHV-6B does have mild pathogenicity, the majority of the population is infected with HHV-6B in childhood, and can therefore be assumed to be able to contain a second HHV-6B infection. If there is a concern that an individual has not previously been exposed to HHV-6B, and may therefore have trouble containing a first HHV-6B infection, particularly if the patient is an adult, the individual can be tested to ensure he or she is seropositive for HHV-6B before administration. If the patient is indeed seronegative for HHV-6B, an alternate virus or an attenuated virus can be used instead. In most embodiments, it is anticipated that non-pathogenic, attenuated, or killed virus will be used.

In all cases, to be suitable, the virus should upregulate production of one or more of the HIV-suppressive chemokines RANTES, MIP-1α, and MIP-1β. The upregulation of production of these chemokines in lymphoid tissue creates a high local concentration of the chemokines, increasing the chance that they will contact CCR5 receptor bearing T cells and block the R5 receptor, thereby inhibiting HIV binding and cell entry. Moreover, since lymphoid tissue-tropic herpesviruses have evolved to infect lymphoid tissues, they are able naturally to target and infect the correct tissues.

Of course, if the patient does eventually progress to AIDS, even a normally non-pathogenic microbe could become a threat to patient health. For added safety, therefore, the viruses used in the methods, uses and compositions of the invention can be attenuated. Live attenuated viruses have been widely used in medicine for vaccination for decades and have strong records of safety. Of the 15 viral vaccines which were FDA approved as of 1996, 11, including vaccines against polio, adenovirus, measles, mumps, rubella, yellow fever, vaccinia, and varicella, used attenuated live virus. There is thus considerable experience in the field in attenuating viruses for use as or in vaccines.

Traditionally, viruses are attenuated by serial passage in culture or in a non-natural host, and virulence is then tested until an appropriate degree of attenuation is achieved, while immunogenicity is retained. See generally, Murphy and Chanock, in: *Fields Virology*, supra. More recently, it has become possible to attenuate viruses by recombinant means. Conveniently, this can be accomplished by deleting some or all of one or more genes required for virulence or pathogenicity of the virus. See, e.g., U.S. Pat. No. 6,004,799 (attenuation of FIV). Alternatively, this can be accomplished by introducing a missense mutation, or by introducing mutations into non-coding regions of the genome that contain cis-acting elements needed for efficient replication. See generally, Murphy and Chanock, in *Fields Virology*, supra. Thus, for example, a herpesvirus of choice can be attenuated by either traditional or by recombinant techniques and used in the compositions and methods of the invention.

Evidence suggests that inactivated (or "killed") viruses retain the ability to upregulate production of cytokines. Thus, in some embodiments, viruses useful in the methods and compositions of the invention can be killed or inactivated and administered to upregulate chemokine production. In some embodiments, the virus is cultured and then killed by formalin. See, e.g., Murphy and Chanock in Fields Virology, supra. In preferred embodiments, the virus is inactivated by ultraviolet light or other methods which permit retention of ligands for cellular receptors so that the virus retains its normal tissue tropism and specificity. Any particular inactivated or killed virus can be tested for its ability to upregulate chemokine production by the assays taught in the Examples, below.

Use of Viral Proteins and Nucleic Acids Encoding them

In some embodiments, proteins of a herpesvirus are used to increase chemokine production. The particular protein or proteins responsible for upregulating production of the CCR5-chemokine can be readily determined by expressing the proteins recombinantly and testing the proteins in the assays provided in the Examples. The proteins can be administered directly into lymphoid tissue. For example, the protein or proteins can be lyophilized and introduced into lymphoid tissue using so-called "needleless" or "biolistic" devices. Similarly, nucleic acids encoding the protein or proteins can be introduced by such devices or by so-called "gene guns."

In patients who still have their tonsils, the nucleic acids or proteins can be administered by direct injection into the tonsils. Where the tonsils are absent, thus eliminating an easy route of administration to lymphoid tissue, the proteins or nucleic acids can be administered by any of a number of alternative methods, including encapsulating the agent in a liposome targeted by antibodies to or ligands for receptors on the target cells. For example, to target the liposome to lymphoid tissue, ligands for the CD4, CD3, or CD45 receptors can be used.

It should be noted that the pathogenicity or tissue tropism of the wildtype herpesvirus is not an issue when using recombinant or isolated herpesvirus proteins or nucleic acids encoding them to trigger increased chemokine production. Therefore, protein or nucleic acid encoding a protein used in the compositions and methods of the invention can be, but do not have to be, from a lymphoid tissue-tropic herpesvirus.

DEFINITIONS

Units, prefixes, and symbols are denoted in their Système International de Unites (SI) accepted form. Unless otherwise indicated, terms used herein have their ordinary meaning as understood by persons of skill in the art. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

"Human herpes virus-6" and "HHV-6" refer to a member of the Betaherpesvirus subfamily discovered by Salahuddin et al. in 1986. See, Pellett and Black, "Human Herpesvirus 6" in Fields et al., eds., *Fields Virology*, Lippincott Williams and Wilkins, Philadelphia Pa. (3rd ed., 1996). The genome of HHV-6 has been sequenced and is publicly available from the National Center for Biotechnology Information (NCBI) of the National Library of Medicine of the National Institutes of Health on-line at the web address of ncbi.nlm.nih.gov, under accession number NC_001664. See also, Gompels et al., Virology 209:29-51 (1995).

"Human herpes virus-7" and "HHV-7" refer to a member of the herpesvirus family discovered in the course of studies on HHV-6. See, e.g., Frenkel and Roffman, "Human Herpesvirus 7" in Fields et al., eds., *Fields Virology*, Lippincott Williams and Wilkins, Philadelphia Pa. ($3^{rd}$ ed., 1996). The genome of HHV-7 has been sequenced and is available from the NCBI at the website noted above, under accession number NC_001716. See also, Pfeiffer et al., J. Virol 69(6)3490-3500 (1995).

References herein to "HIV" refer to HIV-1 unless otherwise specified or required by context.

"Lymphoid tissue-tropic herpesvirus" is used herein to refer to members of the herpesvirus family that can infect cells of the lymphoid tissue, or lymphocytes, or both. For purposes of this application, both HHV-6 and HHV-7 are considered lymphoid tissue-tropic herpesviruses.

"Attenuated virus" refers to a virus that has been altered to be less pathogenic than a wild-type virus of the same species. The attenuation can be by serial passage in a culture or in a non-natural host, which introduces genetic mutations into the organism, or by molecular biological methods, e.g. restriction endonuclease and ligase treatment, which delete some or all of specific genes required for virulence or pathogenicity. Viruses attenuated by the latter methods may also be referred to herein as "attenuated recombinant viruses."

"RANTES" refers to an 8 kD polypeptide belonging to the cysteine-cysteine "CC" or beta-chemokine subfamily. See, e.g., Schell, T., Cytokine 3:165 (1991).

"MIP-1$\alpha$" is a 8 kD polypeptide that is also a member of the CC chemokine subfamily; it is closely related to RANTES. See, e.g., Schell, supra.

"MIP-1$\beta$" is also a member of the CC chemokine subfamily. See, e.g., Schell, supra.

"Nonstructural viral proteins" are those proteins that are needed for viral production but are not necessarily found as components of the viral particle. They include DNA binding proteins and enzymes that are encoded by viral genes but which are not present in the virions.

"Nucleic acid-based vaccines" include both naked DNA and vectored DNA (within a viral capsid) where the nucleic acid encodes viral proteins which produce or which upregulate HIV-suppressive chemokines, such as RANTES.

"Plasma" refers to the fraction of whole blood resulting from low speed centrifugation of EDTA- or heparin-treated blood.

"Pharmaceutically acceptable" refers to a generally non-toxic, inert, and/or physiologically compatible composition.

"Replication" refers herein to replication of a virus in a tissue or the body, unless required by context to refer to replication within an individual cell.

A "retrovirus" is a virus containing an RNA genome and an enzyme, reverse transcriptase, which is an RNA-dependent DNA polymerase that uses an RNA molecule as a template for the synthesis of a complementary DNA strand. The DNA form of a retrovirus commonly integrates into the host-cell chromosomes and remains part of the host cell genome for the rest of the cell's life.

"Structural viral proteins" are those proteins that are physically present in the virus. They include the capsid proteins and enzymes that are loaded into the capsid with the genetic material. Because these proteins are exposed to the immune system in high concentrations, they are considered to be the proteins most likely to provide an antigenic and immunogenic response. Proteins are meant to include both the intact proteins and fragments of the proteins or peptides which are recognized by the immune cell as epitopes of the native protein.

"Viral load" is the amount of virus present in the blood of a patient. Viral load is also referred to as viral titer or viremia. Viral load can be measured in variety of standard ways.

Monitoring Immune Function and Viral Load

CD4+ T Cell Counts

Assessing the immune system of an HIV patient before antiviral treatment and after treatment as well as to determine if a claimed regimen is working is typically performed by measuring CD4+ T cell counts. A detailed description of this procedure was published by Janet K. A. Nicholson et al. 1997 *Revised Guidelines for Performing CD4+ T-Cell Determinations in Persons Infected with Human Immunodeficiency Virus (HIV)* in *The Morbidity and Mortality Weekly Report*, 46(RR-2), Feb. 14, 1997, Centers for Disease Control.

In brief, most laboratories measure absolute CD4+ T-cell levels in whole blood by a multi-platform, three-stage process. The CD4+ T-cell number is the product of three laboratory techniques: the white blood cell (WBC) count; the percentage of WBCs that are lymphocytes (differential); and the percentage of lymphocytes that are CD4+ T-cells. The last stage in the process of measuring the percentage of CD4+ T-lymphocytes in the whole-blood sample is referred to as "immunophenotyping by flow cytometry."

"Immunophenotyping" refers to the detection of antigenic determinants (which are unique to particular cell types) on the surface of WBCs using antigen-specific monoclonal antibodies that have been labeled with a fluorescent dye or fluorochrome (e.g., phycoerythrin [PE] or fluorescein isothiocyanate [FITC]). The fluorochrome-labeled cells are analyzed by using a flow cytometer, which categorizes individual cells according to size, granularity, fluorochrome, and intensity of fluorescence. Size and granularity, detected by light scattering, characterize the types of WBCs (i.e., granulocytes, monocytes, and lymphocytes). Fluorochrome-labeled antibodies distinguish populations and subpopulations of WBCs.

Systems for measuring CD4+ cells are commercially available. For example Becton Dickenson's FACSCount System automatically measure absolutes CD4+, CD8+, and CD3+ T lymphocytes. It is a self-contained system, incorporating instrument, reagents, and controls.

Viral Titer

There are a variety of ways to measure viral titer in a patient (reviewed in *Report of the NIH To Define Principles of Therapy of HIV Infection* as published in the; *Morbidity and Mortality Weekly Reports*, Apr. 24, 1998, Vol 47, No. RR-5, Revised Jun. 17, 1998). It is known that HIV replication rates in infected persons can be accurately gauged by measurement of plasma HIV concentrations.

HIV RNA in plasma is contained within circulating virus particles or virions, with each virion containing two copies of HIV genomic RNA. Plasma HIV RNA concentrations can be quantified by either target amplification methods (e.g. quantitative RT polymerase chain reaction (RT-PCR), Amplicor HIV Monitor assay, Roche Molecular Systems; or nucleic acid sequence-based amplification, (NASBA®), NucliSens™ HIV-1 QT assay, Organon Teknika) or signal amplification methods (e.g., branched DNA (bDNA), Quantiplex™ HIV RNA bDNA assay, Chiron Diagnostics). The bDNA signal amplification method amplifies the signal obtained from a captured HIV RNA target by using sequential oligonucleotide hybridization steps, whereas the RT-PCR and NASBA® assays use enzymatic methods to amplify the target HIV RNA into measurable amounts of nucleic acid product. Target HIV RNA sequences are quantitated by comparison with internal or external reference standards, depending upon the assay used.

Administration of Proteins and Nucleic Acids

Proteins of the virus or nucleic acids encoding them can be used to increase production of HIV-suppressive chemokines. In some embodiments, the proteins or nucleic acids encoding them are administered by biolistic devices. Such devices typically accelerate a particle, such as a gold particle coated with a nucleic acid of interest, directly into a tissue of interest. Gene guns typically accelerate a liquid containing a nucleic acid, or a dry formulation containing the nucleic acid, into the tissue by gas pressure. Such DNA can be in the form of a plasmid, can be so-called "naked" DNA, and can be circular or linearized. In some embodiments, the nucleic acids are stabilized with an excipient, often a carbohydrate such as trehalose, and may be lyophilized. Methods and devices for transfecting cells that may be utilized in the uses and methods of the present invention are well known in the art and are taught in, for example, Felgner, et al., U.S. Pat. No. 5,703, 055; Furth and Hennighausen, U.S. Pat. No. 5,998,382; Falo et al., WO 97/11605; Erdile et al., WO 99/26662; and Donnelly et al., WO 99/52463. See also, Sakaguchi et al., WO 96/12808; Volkin et al., WO 97/40839; and Robinson et al., WO 95/20660. A variety of methods are known in the art for formulating microparticles suitable for needleless injection into a tissue. See, e.g., Osborne, WO 00/13668. DNA expression vectors for direct introduction of DNA into patient tissues can additionally be complexed with other components such as peptides, polypeptides and carbohydrates. Expression vectors can also be complexed to particles or beads that can be administered to an individual, for example, using a vaccine gun.

The proteins or nucleic acids encoding them can be administered by methods well known in the art as described in Donnelly et al. (*Ann. Rev. Immunol.* 15:617-648 (1997)); Felgner et al., U.S. Pat. No. 5,580,859; and Carson et al. U.S. Pat. No. 5,679,647, each of which is incorporated herein by reference. One skilled in the art would know that the choice of a pharmaceutically acceptable carrier, including a physiologically acceptable compound, depends, for example, on the route of administration of the expression vector.

For example, naked DNA or polynucleotide in an aqueous carrier can be injected into tissue, such as the tonsils, in amounts of from 10 μl per site to about 1 ml per site. The concentration of polynucleotide in the formulation is from about 0.1 μg/ml to about 20 mg/ml.

The proteins or nucleic acids encoding them can also be incorporated, if desired, into liposomes, microspheres or other polymer matrices (see, e.g., Felgner et al., U.S. Pat. No. 5,703,055; Gregoriadis, Liposome Technology, Vols. I to III (2nd ed. 1993). Liposomes, for example, which consist of phospholipids or other lipids, are nontoxic, physiologically acceptable and metabolizable carriers that are relatively simple to make and administer. Liposomes include emulsions, foams, micelles, insoluble monolayers, liquid crystals, phospholipid dispersions, lamellar layers and the like.

The proteins or nucleic acids encoding them can also be administered by liposome carriers. Liposome carriers can serve to target lymphoid tissue, as well as to increase the half-life of the composition. In these preparations the protein or nucleic acid to be delivered is incorporated as part of a liposome, alone or in conjunction with a molecule which binds to, e.g., a receptor prevalent among cells in lymphoid tissue. Conveniently, the receptor targeted can be CCR5, since cells to which such liposome bind will also be protected from CCR5-tropic HIV-1 binding and entry during the time the liposomes are bound.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., Ann. Rev. Biophys. Bioeng. 9:467 (1980), U.S. Pat. Nos. 4,235,871, 4,501,728, 4,837,028, and 5,019,369.

Administration of Viruses

The choice of administration procedure for wildtype, attenuated, or attenuated recombinant virus is not critical. Vaccine compositions (e.g., compositions containing the virus) can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular patient, and the route of administration.

For example, attenuated HHV-6A is inoculated, more than once, by the intramuscular route at a dose of about $10^8$ pfu per inoculation, for a patient of 170 pounds. The vaccine can be delivered in a physiologically compatible solution (or "pharmaceutically acceptable" carrier) such as sterile phosphate buffered saline (PBS) solution in a volume of, e.g., one ml. The dose can be proportional to weight. The compositions can be administered to pediatric patients in need thereof in the judgment of the practitioner, and will be especially useful for children infected with HIV at birth. It would not be unexpected for the practitioner to conclude that delaying or inhibiting progression to ADS in a pediatric patient outweighs any concerns over introducing a herpesvirus into the subject.

The compositions can be administered alone, or can be co-administered or sequentially administered with other immunological, antigenic, vaccine, or therapeutic compositions. Such compositions can include other agents to potentiate or broaden the anti-HIV effect.

Other compositions that can be co-administered can include purified antigens from immunodeficiency virus or antigens that are expressed by a recombinant vector system which is able to produce other therapeutic compositions. Co-administration is performed by taking into consideration such known factors as the age, sex, weight, and condition of the particular patient, and, the route of administration.

The viruses can be delivered via a variety of routes. Typical delivery routes include parenteral administration, e.g., intradermal, intramuscular or subcutaneous routes. Other routes include oral administration, intranasal, and intravaginal routes. In a preferred embodiment, the viruses are introduced into the tonsils of patients in which they have not been removed. In the case of HHV-6 and 7, which are believed to reside at least in part in the salivary glands, administration may be accomplished simply by use of a mouth rinse or wash which the subject "swishes" around the mouth for a period of time.

The viruses can also be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, mouth wash, or by aerosol administration by nebulizer, include aqueous or oily solutions. Nasal administration of AIDS-related vaccines is discussed in the following patents, which contain information useful in administering viruses useful in the methods and compositions of the present invention: U.S. Pat. Nos. 5,846,978, 5,663,169, 5,578,597, 5,502,060, 5,476,874, 5,413,999, 5,308,854, 5,192,668, and 5,187,074.

Examples of virus compositions of use for the invention include liquid preparations, for orifice, e.g., oral, nasal, anal, vaginal, etc. administration, such as suspensions, syrups or elixirs; and, preparations for parenteral, subcutaneous, intradermal, intramuscular or intravenous administration (e.g., injectable administration) such as sterile suspensions or emulsions. In such compositions the viruses can be in admixture with a suitable carrier, diluent, or excipient such as sterile water, physiological saline, glucose or the like.

The viruses can also be incorporated, if desired, into liposomes, microspheres or other polymer matrices (see, e.g., Felgner et al., U.S. Pat. No. 5,703,055; Gregoriadis, *Liposome Technology*, Vols. I to III (2nd ed. 1993). Liposomes, for example, which consist of phospholipids or other lipids, are nontoxic, physiologically acceptable and metabolizable carriers that are relatively simple to make and administer. Liposomes include emulsions, foams, micelles, insoluble monolayers, liquid crystals, phospholipid dispersions, lamellar layers and the like.

EXAMPLES

The following examples are offered to illustrate, but not to limit the claimed invention.

Example 1

This Example sets forth materials and methods used in the studies reported in Example 2.

Tissue Culture and Viral Infection

Human tonsils surgically removed during routine tonsillectomy and not required for clinical purposes were received within five hours of excision. Tonsils were dissected into 3-mm blocks and cultured as described earlier (Glushakova, S. et al., *Nature Med.* 1: 1320-1322 (1995); Grivel, J. C. et al., *Nature Med* 5:344-6 (1999)). The protocol for infection with different HIV-1 isolates (received through the AIDS Research and Reagent Program, Division of AIDS, NIAD, NIH) has been described previously (Glushakova, S. et al., *Nature Med.* 1:1320-1322 (1995); Grivel, J. C. et al., *Nature Med*, supra). For HHV-6 infection, each tissue block was inoculated overnight with 10 μL of viral stock containing approximately $10^6$ cell culture infectious doses per mL, as determined by titration of infectivity on primary human PBMC. The viral stock was produced by infecting PHA-activated human PBMC with HHV-6 and by collecting the cell-free culture supernatant at the time of peak cytopathic effect (around days 6-8 post-infection). For coinfection, the tissue blocks were infected overnight with HHV-6, then the medium was changed and the blocks were inoculated with 5 μL of HIV-1 stocks containing approximately $10^5$ pg of p24 antigen per mL. The medium was changed every three days. Additional details of the culture method have been previously described (Glushakova, S. et al., *Nature Med.* 1:1320-1322 (1995); Grivel, J. C. et al., *Nature Med*, supra).

Evaluation of Viral Replication and Chemokine Production

Productive HIV-1 infection was assessed by measuring p24 concentration in culture medium using a commercial kit (Beckman-Coulter, Miami, Fla.). HHV-6 viral load was determined in tissue culture medium and cellular DNA extracted by the chloroform-phenol method using a quantitative calibrated real-time PCR system (Locatelli, G. et al. *J. Clin. Microbiol.* 38:4042-8 (2000)). Coinfection with two HIV-1 variants was evaluated by quantitative real-time PCR using the ABI-PRISM 7700 Sequence Detector (PE Applied Biosystems, Foster City, Calif.). Viral RNA was extracted using a QIAamp Viral RNA Kit (QIAGEN GmbH, Hilden, Germany). The specific primers sets used to detect SF162 and LAV.04 were the following: SF162 forward, 5'-TATGCAA-CAGGAGACATAATAGGAGATATAAG-3' (SEQ ID NO:1); SF162 reverse, 5'-TAGTTCCATTAGTGTTATTTG-GCCCTATAG-3' (SEQ ID NO:2), LAV.04 forward, 5'-GT-TACAATAGGAAAAATAGGAAATATGAGACA-3' (SEQ ID NO:3); LAV.04 reverse, 5'-TCACTTCCTTCAGTGT-TATTTGACCCTTC-3' (SEQ ID NO:4). The reaction mixture contained SYBR Green PCR master mix, 300 nM of each primer, and 10 µL of cDNA. Following activation of the AmpliTaq Gold for 10 min at 95° C., 40 cycles of 15 sec at 95° C. and 1 min at 60° C. were carried out. A reference standard curve was obtained using serially diluted plasmids containing the target genes.

The levels of MIP-b 1α, MIP-1β and RANTES were evaluated in culture medium and in tissue blocks by ELISA, using standards and both capture and detection antibodies from R&D systems (Minneapolis, Minn.) according to the manufacturer's recommendations. ELISA data were acquired and analyzed with Delta Soft 3 (BioMetallics, Princeton, N.J.) using a four-parameter fitting algorithm.

Example 2

We utilized a well-defined model system for the study of HIV-1 infection in lymphoid tissue, based on human tonsillar tissue blocks cultured ex vivo without exogenous stimulation or activation (Glushakova, S. et al., *Nature Med.*, supra); Grivel, J. C. et al., *Nature Med*, supra). Recently, we found that this system can also support productive infection by HHV-6. Inoculation of tissue blocks with the GS strain (subgroup A) of HHV-6 (Salahuddin, S. Z. *Science* 234:596-601 (1986)) resulted in productive infection, as assayed by quantitative calibrated real-time PCR (Locatelli, G. et al. *J. Clin. Microbiol.* 38:4042-8 (2000)). Flow cytometry of cells isolated from the infected blocks and stained intracellularly for the HHV-6 nuclear protein p41 confirmed productive infection of the tissue. Viral replication became detectable between days 6 and 9 post-inoculation and progressively increased until day 12, with peak viral production ranging between $6 \times 10^6$ and $2.5 \times 10^9$ viral genome equivalents per mL of culture supernatant.

Figure 1:
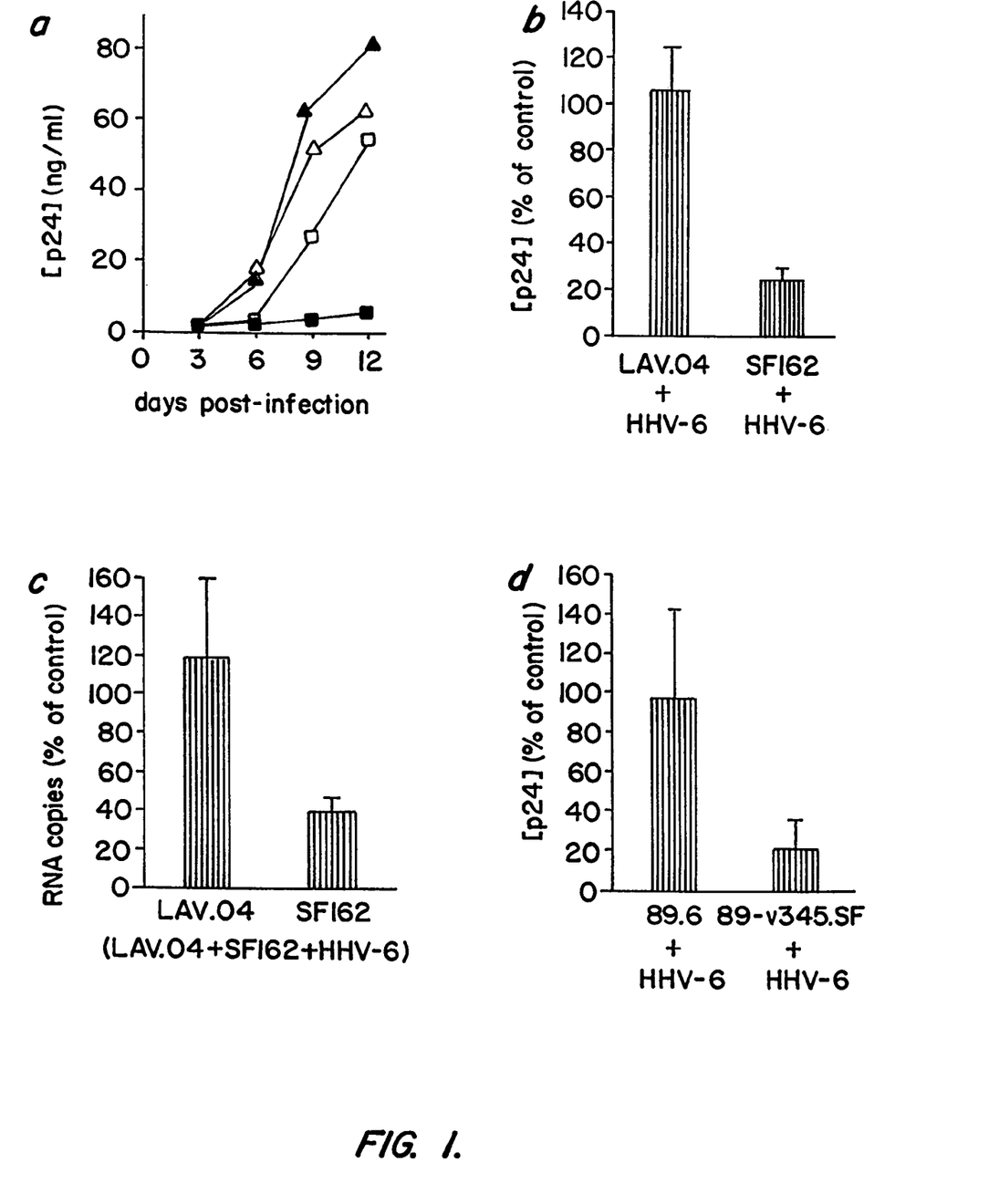
FIG. 1. Differential effect of HHV-6 on replication of HIV-1 of different coreceptor tropism.

As multiple interactions have been documented between HHV-6 and HIV-1 both in vitro and in vivo (Lusso, P. et al., *Immunol Today* 16:67-71 (1995)), we investigated whether these two viruses affect each other within the context of human lymphoid tissue. Groups of 54 matched blocks of human tonsillar tissue, approximately 3 mm thick, each derived from one of 35 donors, were infected with either HHV-6 alone, HIV-1 alone, or HHV-6 and HIV-1 in combination. Two biologically diverse HIV-1 strains were used: LAV.04, a prototypic CXCR4-utilizing variant, and SF162, a prototypic CCR5-utilizing variant. Tissue blocks were first inoculated for 16 h with HHV-6 GS, and then the unbound virus was washed and the blocks were inoculated with HIV-1. As previously documented in this model system (Glushakova, S. et al., *Nature Med.* 1:1320-1322 (1995); Glushakova, S. et al., *AIDS Res.& Hum. Retrovir.* 13:461-471 (1997)), replication of either variant of HIV-1 was first detected approximately at day 6 post-inoculation, as assessed from the levels of p24 release (FIG. 1a). The maximal level of viral replication typically occurred between days 9 and 12. The absolute level of viral replication varied in tissues from different donors, ranging from 5 to 75 ng of p24 per tissue block.

Strikingly, coinfection with HHV-6 differentially affected the replication of different HIV-1 variants. A dramatic suppression of HIV-1 replication was observed in tissues coinfected with HHV-6 and the CCR5-using variant SF162 (viral replication level was 23+5% relative to matched tissues infected by SF162 alone n=10, P=0.006) (FIG. 1a, b). Inhibition of viral replication was typically evident between days 6 and 9 post-HIV infection, reaching the maximal level at day 12. In contrast, there was a slight enhancement in the replication of the CXCR4-using variant LAV.04 in matched tissue blocks (FIG. 1a, b), although it did not reach statistical significance (n=17, P=0.18) due to donor-to-donor variability.

To mimic more closely the situation in vivo, where different HIV-1 variants may coexist, we coinfected tissue blocks from five different donors with HHV-6 and a mixture of SF162 and LAV.04. To discriminate between the replication of CCR5- and CXCR4-tropic variants in the same tissue, we developed a real-time PCR assay with two different sets of primers specific for LAV.04 or SF162. Similarly to the results obtained with individual HIV-1 variants, HHV-6 differentially affected these viruses in the context of the same tissue block. By day 9 post-infection, replication of the CCR5-using HIV-1 variant was significantly inhibited (viral replication level was 40+7% relative to matched tissues not coinfected with HHV-6; n=5, P=0.009) (FIG. 1c). By contrast, the replication of the CXCR4-using variant LAV.04 was slightly enhanced (120+40%; n=5) (FIG. 1c), however, due to donor-to-donor variability, the average increase was not statistically significant (P=0.5).

To definitively prove that the differential effect of HHV-6 on HIV-1 replication was related to HIV-1 coreceptor tropism, we used two isogenic dual-tropic molecular clones, 89.6 and 89-v345.SF. The latter differs from 89.6 only for sequences in the gp120 V3-V5 region, which were replaced with corresponding sequences from SF162 (Smyth, R. J. et al., *J. Virol.* 72:4478-84 (1998)). In ex vivo human lymphoid tissue 89.6 and 89-v345.SF behave as CXCR4- or CCR5-tropic variants, respectively (Glushakova, S. et al. *J. Clin. Invest.* 104:R7-R11 (1999)). In agreement with our results with uncloned HIV-1 isolates, HHV-6 coinfection of lymphoid tissue resulted in a marked inhibition of 89-v345.SF replication (viral replication level was 21+14% relative to matched tissues not coinfected with HHV-6) and did not affect 89.6 replication (viral replication level was 99+43% relative to matched tissues not coinfected with HHV-6) (FIG. 1d).

Next, we measured the level of HHV-6 replication in HIV-1 coinfected tissues. In two out of five analyzed donors, coinfection with SF162 caused approximately 50% enhancement of HHV-6 replication relative to tissues infected with HHV-6 alone, whereas in tissues from the three other donors there was no stimulation of HHV-6 production. Coinfection with LAV.04 caused a 25% to 80% reduction of HHV-6 replication in tissues from three of the five analyzed donors, whereas in the other donors there was either no effect or a slight enhancement. For both viruses, the overall difference in HHV-6 replication in HIV-coinfected and control tissues was not statistically significant (P=0.45 and P=0.62, respectively).

To investigate the potential mechanisms underlying the effects of HHV-6 on HIV-1 infection, we evaluated the production of RANTES, MIP-1α and MIP-1β, the three CC chemokines that bind CCR5, as they were reported to cause similar effects on the replication of different HIV-1 strans (Kinter, A. L. et al. *Proc. Natl. Acad. Sci. USA* 93:14076-81 (1996); Margolis, L. B. et al., *J. Clin. Invest.* 101:1876-80 (1998); Gordon, C. J. et al. *J. Virol.* 73:684-94 (1999)). In all the tissues infected with HHV-6, either alone or in combination with HIV-1, we documented a dramatic increase in the production of RANTES (FIGS. 2*a,b*), whereas the levels of MIP-1α and MIP-1β were not significantly augmented (not shown). Regression analysis demonstrated a significant correlation between HHV-6 replication and RANTES upregulation ($R=0.66$, $P=0.004$). In contrast to HHV-6-infected tissue, there was no significant upregulation of RANTES if the cells were isolated from the tonsillar tissue and then infected with HHV-6 (not shown), indicating that the tissue context is critical for this upregulation. The increase in RANTES production in HHV-6-infected tissues became evident at day 6 post-infection and continued throughout the course of the experiments (FIG. 2*a*).

Figure 2:
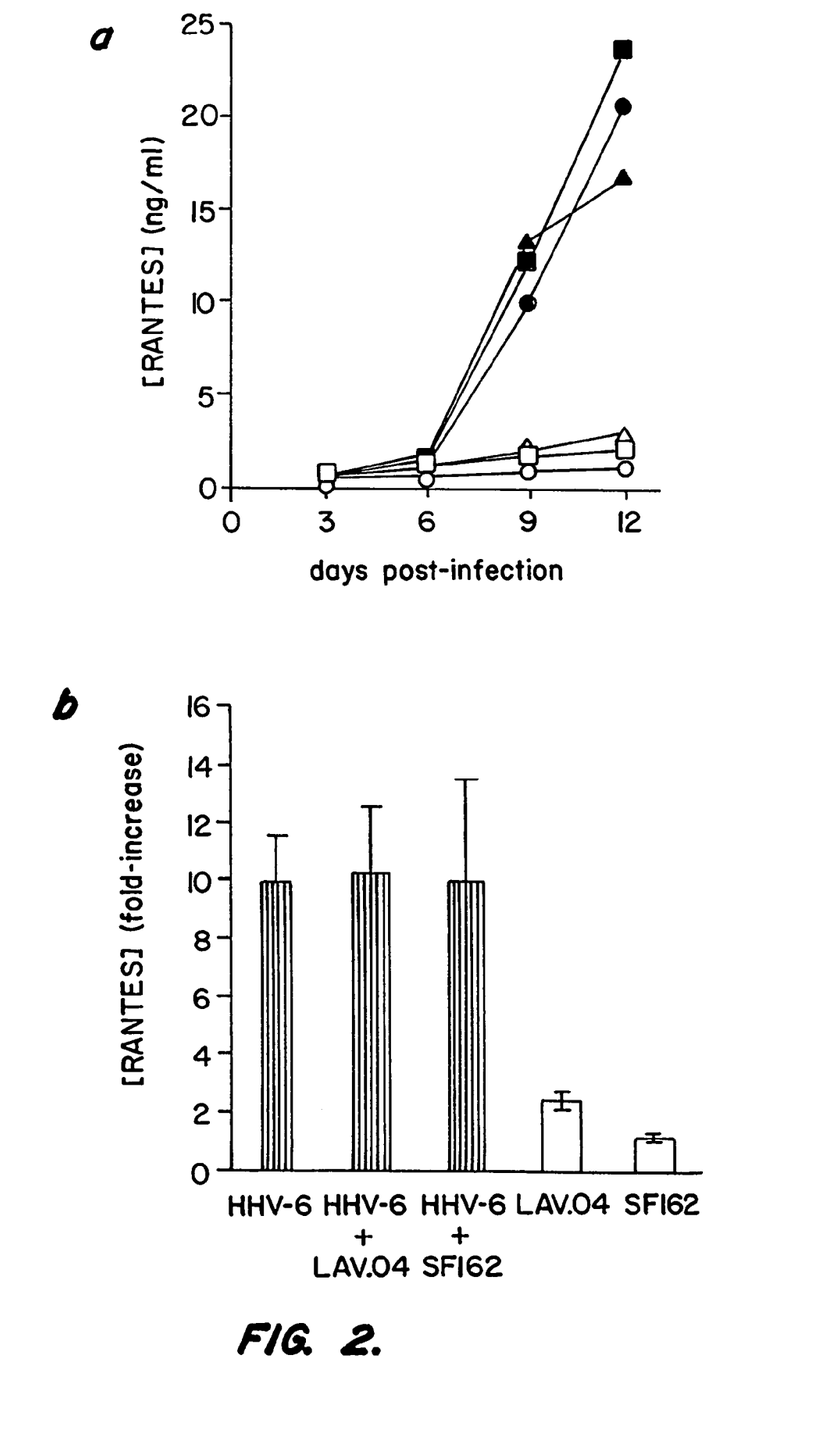
FIG. 2. Production of RANTES in human lymphoid tissues infected ex vivo with HHV-6 alone or in combination with either CCR5- or CXCR4-tropic HIV-1.

FIG. 2*b* summarizes data obtained with tissues from 34 different donors: the mean increase in RANTES was 10+2-fold ($P=6\times10^{-5}$) relative to matched uninfected controls. Flow cytometry of cells isolated from HHV-6-infected tissue blocks also documented increased numbers of RANTES-producing cells; interestingly, about one third of these RANTES-producing cells were HHV-6 p41-negative. The production of RANTES was similarly increased in tissues coinfected with HHV-6 and either LAV.04 (10+3-fold, n=17, $P=1.2\times10^{-3}$) or SF162 (10+3-fold, n=10, $P=1.5\times10^{-3}$). There was a significant correlation between HHV-6-induced RANTES upregulation and suppression of SF162 replication ($R=0.94$, $P=0.002$).

Figure 3:
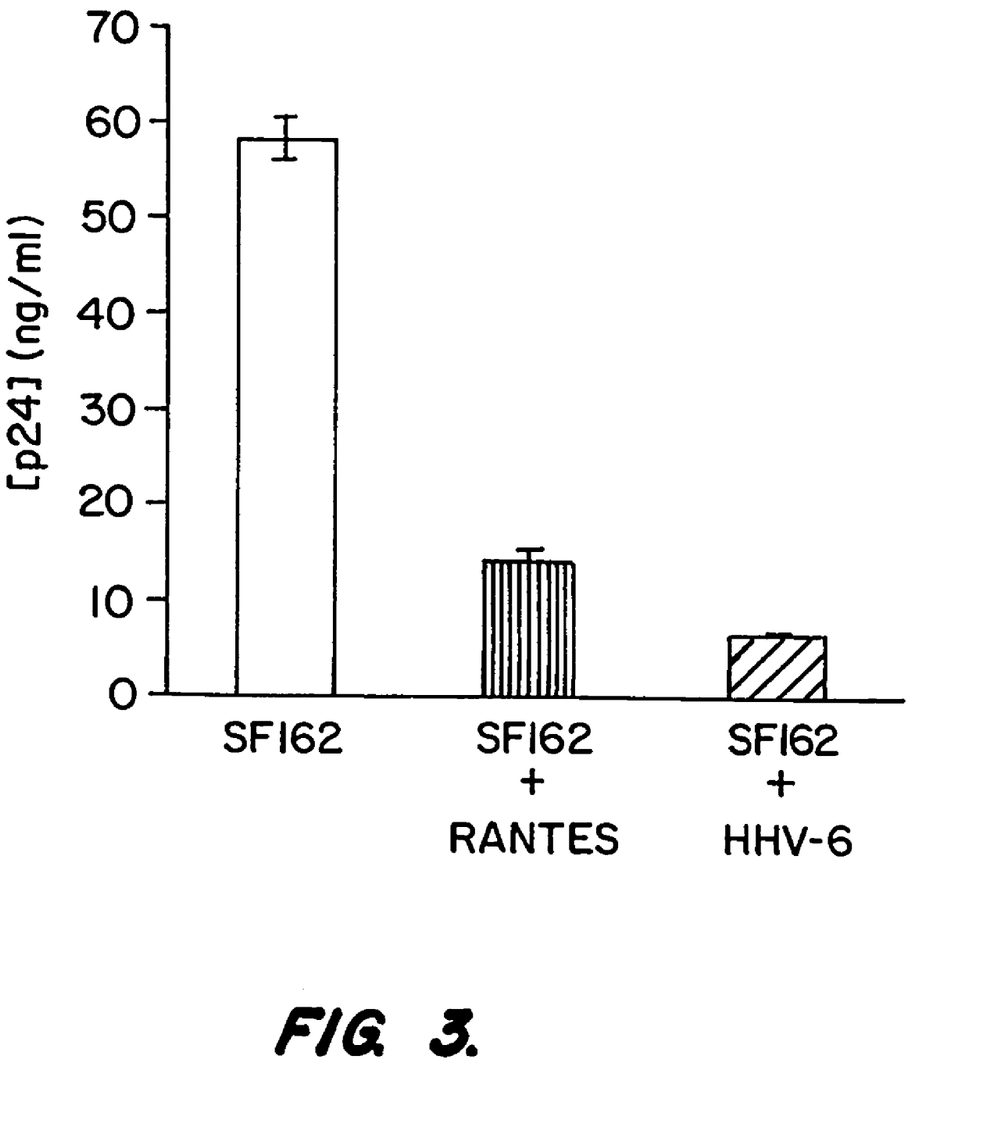
FIG. 3. Suppression of CCR5-tropic HIV-1 replication by RANTES in human lymphoid tissue. Replication of SF162 HIV-1 in matched tissues treated with exogenous RANTES (40 nM) or coinfected with HHV-6. Each bar represents the mean+S.E.M of RANTES production in 54 pooled blocks from a single donor.

Next, we attempted to determine whether the levels of HHV-6-induced RANTES are sufficient to inhibit replication of CCR5-tropic HIV-1 and whether this effect of HHV-6 could be mimicked by exogenous RANTES. While the average amount of endogenous RANTES released into the medium by HHV-6-infected tissues was 0.83+0.2 nM (median 0.3 nM) (n=35), approximately 10-fold higher levels were detected inside the tissue blocks ($P=0.004$). Conversely, addition of exogenous RANTES resulted in an opposite gradient, with a concentration inside the tissue approximately 13-fold lower than outside ($P=0.014$). Based on these measurements, we estimated that exogeneous RANTES in the range of 10 to 100 nM would result in tissue levels similar to those induced by HHV-6 infection. Therefore, we compared exogenous RANTES at 40 nM with HHV-6 for their ability to suppress SF162 replication in matched tissue blocks. As shown in FIG. 3, RANTES inhibited SF162 replication approximately to the same extent as did HHV-6. This result is in agreement with our previous demonstration of the inhibitory effect of RANTES at 100 nM on the replication of CCR5-using HIV-1 variants in lymphoid tissue (Margolis, L. B. et al., *J. Clin. Invest.* 101:1876-80 (1998)).

Our results demonstrate that HHV-6 dramatically influences HIV-1 infection in human lymphoid tissue, with a differential effect on CCR5- and CXCR4-tropic HIV-1 variants. This was shown with both monotropic HIV-1 strains and dual-tropic isogenic molecular clones that, in tissues, use predominantly only one of the coreceptors. Moreover, we identified a mechanism, namely, an increased production of the CC-chemokine RANTES, whereby HHV-6 selectively suppresses the replication of CCR5-utilizing HIV-1. Upregulation of endogenous RANTES by HHV-6 can also explain why in tissues from some donors HHV-6 enhanced the replication of CXCR4-tropic HIV-1, since exogenous RANTES was shown to exert a similar effect in lymphocyte cultures (Kinter, A. et al. *Proc. Natl. Acad. Sci. USA* 95:11880-5 (1998); Kelly, M. D. et al., *J. Immunol.* 160:3091-95 (1998); Dolei, A. et al. *AIDS* 12:183-90 (1998)). Although HHV-6-induced RANTES upregulation seems to be sufficient to account for the observed modulation of HIV replication in lymphoid tissue, other mechanisms could also play a role. For example, HHV-6-induced modulation of either CCR5 or CXCR4 expression could result in altered HIV-1 replication. However, HHV-6 infection did not result in significant changes in either CCR5 or CXCR4 expression. Moreover, the two HHV-6-encoded G-protein-coupled receptors (GPCR), U12 and U51, are not functional as HIV coreceptors (Rucker, J. et al. *J. Virol.* 71:8999-9007 (1997)), and thus their expression could not affect HIV-1 infection. HHV-6 GPCR could also influence HIV replication indirectly by inducing constitutive cell activation, as was shown for HHV-82 (Arvanitakis, L. et al., *Nature* 385:347-50 (1997)), and thereby possibly upregulating chemokines, including RANTES. However, such activation was never demonstrated for HHV-6, and moreover, expression of HHV-6 GPCR U51 was shown to decrease extracellular RANTES due to chemokine sequestration (Milne, R. S. et al. *J. Immunol.* 164:2396-404 (2000)).

Regardless of the mechanisms involved, our observations indicate that HHV-6 replication, an event that frequently occurs in vivo during the progression of HIV-1 disease (Lusso, P. et al., *Immunol Today* 16:67-71 (1995)), may profoundly influence the course of HIV-1 infection by selectively suppressing CCR5-utilizing HIV-1 variants, while not affecting or even stimulating replication of CXCR4-tropic variants, and thus may be relevant to the HIV coreceptor switch. Our results provide the first demonstration that another viral agent can selectively affect HIV-1 infection.

In light of the results reported herein, and in light of the similar protein composition of the herpesviruses in general, it is expected that other human herpesviruses have the ability to modulate HIV-1 replication.

Example 3

This Example discusses the results of the studies described above.

In the studies above, we show that in human lymphoid tissue ex vivo (Glushakova, S. et al., *Nature Med.* 1995, supra); Glushakova, S. et al., *AIDS Res. & Hum. Retrovir.* 13:461-471 (1997); Grivel, J. C. et al., *Nature Med*, supra) HHV-6 affects HIV-1 infection in a coreceptor-dependent manner, dramatically suppressing CCR5-tropic but not CXCR4-tropic HIV-1 replication, as documented with both uncloned viral isolates and isogenic molecular chimeras. Furthermore, we demonstrate that HHV-6 markedly increases the production of the CCR5 ligand RANTES, the most potent HIV-inhibitory CC chemokine (Cocchi, F. et al. *Science* 270: 1811-5 (1995)), and that exogenous RANTES mimics the effects of HHV-6 on HIV-1, providing a mechanism for the selective blockade of CCR5-tropic HIV-1. Our data suggest that HHV-6 can profoundly influence the course of HIV-1 infection.

Example 4

This Example sets forth the materials and methods used in the studies reported in Example 5.

Tissue Culture and Infection

Human tonsils surgically removed during routine tonsillectomy and not required for clinical purposes were received within five hours of excision. Tonsils were dissected into 3-mm blocks and cultured as described earlier (Glushakova (1995); Grivel (1999)). For HHV-6 infection, the tissue blocks were either inoculated overnight with 10 µL of viral stock pipetted onto the external surface of each fragment or soaked in the undiluted viral stock for 4 hrs., and then washed with complete culture medium. The viral stocks contained approximately $10^6$ cell culture infectious doses per ml, as determined by titration of infectivity on primary human PBMC. The viral stocks were produced as previously described (Lusso, P. et al., *J. Exp. Med.* 167:1659-1670 (1988)) by infecting PHA-activated human PBMC (for GS) or CD8-depleted PBMC (for PL1) and by collecting the cell-free culture supernatant at the time of peak virus-induced cytomorphological transformation (around days 6-8 post-infection). The culture medium was changed every three days. Additional details of the culture method have been previously described (Glushakova (1995); Grivel (1999)).

Quantification of HHV-6 DNA by Calibrated Real-Time PCR

DNA extraction from cell-free culture supernatants or from pelleted cells was performed using the phenol-chloroform method. The quantification of HHV-6 DNA was performed using the TaqMan technology on an ABI PRISM 7700 SDS (Applied Biosystems, Foster City, Calif.); a quantitative β-actin detection system (Applied Biosystems) was used to quantify the content of human genomic DNA. At least 1 µg of genomic DNA recovered from each cellular pellet was subjected to real-time PCR analysis. Details about the real-time PCR technique for HHV-6 have been reported elsewhere (Locatelli, G. et al., *Journal of Clinical Microbiology*, 38:4042-4048 (2000)). The primers and the probe were derived from open reading frame U67, which is highly conserved in both subgroups (A and B) of HHV-6. The primers were 5'-CAAAGCCAAATTATCCAGAGCG-3' (SEQ ID NO:5) and 5'-CGCTAGGTTGAGGATGATCGA-3') (SEQ ID NO:6); the probe was 5'-CACCAGACGTCACAC-CCGAAGGAAT-3' (SEQ ID NO:7). The probe was covalently linked with the reporter dye 6-carboxy-fluorescein (FAM) in 5' position and the quencher dye 6-carboxy-tetramethyl-rhodamine (TAMRA) in 3' position. The amplified product was 133 bp in length. The reaction was performed in a total volume of 25 µl, with DATP, dCTP and dGTP at 100 µM each and dUTP at 200 µM, TaqMan buffer A 1×, magnesium chloride 5.5 mM, primers 300 nM each, probe 50 nM, 0.625 units of AmpliTaq Gold, 0.25 units of Uracil-N-glycosylase, 40% V/V of sample DNA. PCR was performed first by activation of the uracyl-N-glycosylase (UNG) (50° C. for 2 min), followed by the AmpliTaq Gold activation (95° C. for 15 min) and by 40 cycles of amplification (denaturation step 15 sec at 95° C.; annealing/extension step 1 min at 60° C.). Data analysis was performed using the Sequence Detection Software (PE Applied Biosystems). As a reference for HHV-6 DNA quantitation, the HHV-6 fragment amplified by the above primers was cloned into the pCRII plasmid (Invitrogen). A standard curve was obtained by serially diluting the plasmid stock quantitated by spectrophotometry. Serial dilutions of genomic DNA purified from PBMC of normal donors were employed to generate a reference curve for β-actin quantitation. The results were normalized using a synthetic DNA calibrator molecule ($10^4$ copies per reaction), added to the samples before the extraction step, which allows to control for intersample extraction efficiency and to monitor PCR artifacts; the calibrator molecule was then coamplified with the HHV-6 target sequence. Primers and calibrator probe were not cross-reactive with the HHV-6 and β-actin sequences.

Flow Cytometry Analysis of Surface and Intracellular Protein Expression

Single cells suspension were prepared from tissue blocks by mechanical dissociation, and cells that emigrated into the collagen sponge were squeezed out at day 13 to 15 post infection. To determine the proportion of infected cells, cells wer stained as follows: The cells were stained with anti-CD56 PE, CD2 Tricolor, anti-CD4 APC or anti-CD8 APC (Caltag Laboratories, Burlingame, Calif.), after cell surface staining cells were permeablized with Fix & Perm (Caltag Laboratories, Supra) and stained with anti-HHV-6 nuclear phosphoprotein (Early nuclear Antigen p41/38 antibody (Advanced Biotechnologies Inc, Columbia, Md.) coupled with Alexa 488 (Molecular Probes, Eugene, Oreg.). The percentage of infected cells is reported for events gated on CD2+, CD56– cells. The determination of the infection of memory and naïve cells was performed as above except that the following antibody combination was used: CD2 PE, CD62L TriColor and CD45 RA APC (Caltag Laboratories) for cell surface staining and anti HHV-6 Np 41 Alexa 488 for intracellular staining.

Determination of surface antigen modulation was performed as follows, cells were stained with CD46 PE (Serotec) CD2 TriColor and CD3 APC, after fixation and permeabilization, cells were stained with anti HHV-6 Np 41 Alexa 488. Median fluorescence intensities of CD3 and CD46 were measured in gated CD2+ cells subgated on HHV6 NP 41. Receptor modulation is expressed as the ratio of the median fluorescence value of cells in infected tissue to that of cells in uninfected control for cells that are positive for HHV-6 antigen and for those that are not.

Quantification of cells were performed as previously described using TrueCount tubes on cells stained for CD3 FITC, CD4 PE, CD8 TriColor. Values were normalized for tissue weight if each experimental group Cytokine and Chemokine Production The levels of MIP-1α, MIP-1β and RANTES were evaluated in culture medium by ELISA, using standards and both capture and detection antibodies from R&D systems (Minneapolis, Minn.) according to the manufacturer's recommendations. ELISA data were acquired and analyzed with Delta Soft 3 (BioMetallics, Princeton, N.J.) using a four-parameter fitting algorithm.

Example 5

Replication of HHV-6A and B in Ex Vivo-Cultured, Structured Human Tonsillar Tissue In an attempt to develop a reliable model system for the study of HHV-6 infection, we tested the ability of different HHV-6 strains to replicate in ex vivo-cultured, structured human lymphoid tissue. This experimental model, which allows for the prolonged culture of small fragments of tonsil, lymph node or appendix tissue at the liquid-air interface, has been previously employed to investigate the pathogenic mechanisms of HIV-1 infection (Glushakova (1995); Grivel (1999)). The tissue fragments were exposed to the virus either by pipetting 10 µl of virus stock onto their external surface or, alternatively, by soaking them in the viral stock for 4 hrs. at 37° C. The viral strains used included HHV-6 GS, a subgroup-A isolate originally derived from a patient with a hematological malignancy (Salahuddin, S. Z. et al., *Science*, supra), and HHV-6 PL1, a subgroup-B isolate obtained from a healthy adult subject. Viral replication was documented by measuring the kinetics of accumulation of both cell-associated and cell-free viral genomes using a quantitative-calibrated real-time PCR assay. Viral antigen expression was assessed by flow cytometry using mAbs directed against one non-structural (p41) and one structural (gH) HHV-6 protein, both of which are expressed late in the viral life cycle and associated with productive infection.

Real-time PCR showed a progressive accumulation of HHV-6 genome equivalents over time in the culture supernatants of infected tissues, with peak levels between 0.9 and $2.44 \times 10^9$ genome equivalents per ml of culture supernatant at day 13 post-infection in tissues infected with HHV-6A (n=3). Similarly, increasing levels of HHV-6 genome equivalents were detected in cell-associated DNA extracted from the same tissues. In parallel, intracellular expression of the p41 viral antigen was detected. In tissues infected with HHV-6 B, p41-antigen expression was consistently lower, with a mean of 6±3% T cells at day 13 (n=3).). Altogether, the data demonstrated that both HHV-6 subgroups productively infect ex vivo-cultured human lymphoid tissue in the absence of exogenous mitogenic or antigenic stimulation.

Although the above results demonstrated that both HHV-6 subgroups can replicate in human lymphoid tissue, they likely provide an underestimation of the total proportion of HHV-6-infected cells. This is not unexpected since secondary lymphoid organs physiologically contain a large population of freely circulating, non-resident cells, predominantly T and B lymphocytes. In this emigrated population, we found that the proportion of viral antigen-expressing cells was consistently higher than in the total cell suspension obtained from the tissues. This phenomenon suggests that infected cells might preferentially escape from the lymphoid tissue into the lymph or blood, thus providing a potential mechanism of virus dissemination throughout the organism.

Primary T-Cell Tropism of HHV-6A and B in Structured Human Lymphoid Tissue.

The lineage origin of the cells productively infected by HHV-6 in lymphoid tissue was investigated by multicolor flow cytometry using mAbs directed against different leukocyte membrane antigens. At day 14 after infection with HHV-6A, a mean of 25±2% CD4+ T cells and 23±4% CD8+ T cells were found to be productively infected in tissues from 5 individuals. In three tissues infected with HHV-6B, productive infection was detected in a mean of 12±6% CD4+ T cells and 7±3% CD8+ T cells. Thus, infection of CD4+ and CD8+ T cells occurred with similar efficiency, although CD8+ T cells were slightly less infected by HHV-6B. However, since CD4+ T cells represent the predominant cell subpopulation in human lymphoid tissue, the absolute number of infected CD4+ T cells was consistently higher than that of CD8+ T cells. Very little, if any, productive HHV-6 infection was detected in B cells and other cell types.

HHV-6-Infected T Cells Express a Memory-Type Phenotype.

Further phenotypic analysis of cells isolated from tissues infected with both HHV-6A and B showed that the majority of p41 antigen-positive T cells expressed a memory-type phenotype, as they failed to express the CD45RA and CD62L antigens. However, expression of CD45RA and CD62L was detected in approximately 13.4%±1.7 and 10.5±1.8% of infected cells in HH6 GS and PL-1 infected tissues respectively. Since we observed that the mean proportion of phenotypically memory cells in uninfected tissues from 5 different donors was 2.6±0.2-fold higher than that of naïve cells, the proportion of HHV-6-infected cells in the two subpopulations seems to reflect their relative abundance in ex vivo-cultured lymphoid tissue.

Cytopathic Effects of HHV-6 in Lymphoid Tissue.

To evaluate the cytopathic effects of HHV-6 in infected lymphoid tissue, we measured the absolute number of cells recovered from pooled tissue fragments using calibrator beads as a volume reference. Flow cytometry using selected surface membrane markers allowed to calculate the absolute numbers of cells belonging to the different subsets. A moderate cell depletion was generally observed at day 12-13 post-infection. Consistent with the phenotype of the infected cells, both HHV-6A and B caused a predominant depletion of CD4+ T cells; however, in tissues infected with HHV-6A, a significant loss of CD8+ T cells was also observed. These data indicate that HHV-6 infection in the context of human lymphoid tissue is cytopathic and that cell depletion involves primarily the cells in which HHV-6 is replicating, without significantly affecting bystander cells. Both cells within the tissue blocks and cells emigrated into the gel-sponge were similarly depleted.

Downmodulation of the CD46 Receptor in HHV-6Infected Lymphoid Tissue.

The CD46 glycoprotein, a member of the regulator of complement activity (RCA) family, is a critical cellular receptor for HHV-6A and B. We investigated whether receptor downmodulation, which is a common sequela of viral infection and was documented in cells infected with HHV-6 in vitro, also occurs in the context of structured lymphoid tissue. Cells from infected and matched uninfected tissues were stained for HHV-6 p41, CD2, CD3 and CD46 expression. A significant downmodulation of CD46 expression was observed in CD2+ T cells obtained from tissues infected with HHV-6A. Interestingly, a loss of CD46 fluorescence intensity was seen both in cells expressing viral antigens (mean reduction: 90±4%) and in bystander T cells (mean reduction: 82±8%; n=5). In contrast, CD46 downmodulation was less pronounced in tissues infected with HHV-6B, with a markedly lower reduction in bystander compared to infected T cells (mean reduction: 17±8 vs. 54±9; n=3). This finding could reflect, at least in part, the overall lower efficiency of infection by HHV-6B in lymphoid tissue. Indeed, a significant correlation was seen between CD46 downmodulation in bystander T cells and viral load (R=0.8, P=0.002), suggesting that receptor engagement by free extracellular virions could be responsible for this phenomenon. Downmodulation of CD46 in bystander cells was further confirmed by analyzing CD46 expression in non-T lymphocytes. In HHV-6A-infected tissues, non-T bystander cells showed a mean decrease in CD46 expression of 80±8%, whereas no significant effect was observed in HHV-6B-infected tissue (0.34±2.6% decrease). These data demonstrate that HHV-6, particularly subgroup A, has the potential to induce an important loss of CD46 in human lymphoid tissue, which could result in an increased susceptibility to tissue damage secondary to spontaneous activation of the complement cascade.

Altered Expression of T-Cell Surface Antigens by HHV-6.

We evaluated by flow cytometry the effects of HHV-6 on the expression of different T-cell surface markers of functional relevance. Similar to CD46 and as previously documented in HHV-6-infected PBMC cultures and clones (Lusso, P. et al., *J. Immunol.* 147:2147-53 (1991)), the CD3 antigen was dramatically downmodulated in tissues infected with both HHV-6A and B. In five HHV-6A-infected tissues, the expression of CD3 was virtually abrogated in HHV-6-expressing cells (mean reduction relative to uninfected controls: 99.3±0.09%). By contrast, in p41 antigen-negative cells, there was only a limited downmodulation of CD3 (mean reduction: 25±2%). Similar results were obtained in three HHV-6B-infected tissues, with a marked downmodulation of CD3 in p41 antigen-positive cells (mean reduction: 99.3±0.15%), but a very low reduction in bystander uninfected cells (mean reduction: 12.5+7.7%). At variance with CD46 downmodulation, there was no correlation between viral load and CD3 down-modulation in bystander cells (r=0.68 P=0.1).

In contrast to CD3, the CD4 antigen was significantly upregulated on the surface membrane of cells isolated from HHV-6-infected tissues. Again, the effect was induced by both A and B viral variants. In tissues infected by HHV-6A, the mean increase in CD4 expression was 170±8% in HHV-6 p41 antigen-positive cells, compared to $CD4^+$ T cells from matched uninfected tissue. By contrast, bystander uninfected $CD4^+$ T cells had a lower CD4 expression (mean reduction: 67.7±5%) compared to $CD4^+$ T cells from uninfected tissue. These data demonstrate that HHV-6 can affect the function of T cells in secondary lymphoid tissues by altering the expression of critical functional surface molecules, such as CD3 and CD4.

Induction of Chemokine Secretion by HHV-6 in Lymphoid Tissue.

Next, we studied the secretion of selected chemokines in HHV-6 infected lymphoid tissue. A selective upregulation of the CC chemokine RANTES was documented with both HHV-6A and HHV-6B. HHV-6A enhanced the secretion of RANTES approximately 9-fold (8.8±2.6 fold; P=0.0009), relative to uninfected control, during the last three days of the experiments. RANTES was also upregulated by HHV-6B, albeit less efficiently (2.0±0.2 fold, relative to matched uninfected controls; P=0.03). Analysis by intracellular staining showed that HHV-6A infection resulted in a 2-fold increase in the number of RANTES-producing cells relative to uninfected controls. The increase was observed in both $CD4^+$ and $CD8^+$ T cells (2.4±0.4 and 2.2±0.3, respectively; n=3). Interestingly, a considerable proportion of RANTES-producing $CD4^+$ and $CD8^+$ T cells were HHV-6 p41 antigen-negative (35% and 33%, respectively), suggesting that bystander T cells were also altered in their secretory activity.

In contrast to the observations with RANTES, HHV-6 caused only a moderate increase in the production of the related CC chemokines MIP-1α and MIP-1β, which failed to reach statistical differences. The mean increase in the levels of MIP-1α in HHV-6A-infected tissues, in comparison with matched uninfected controls, was 3.9±1.3 fold (P=0.27), while the levels of MIP-1β were increased 1.8±0.3 fold (P=0.8). In HHV-6B-infected tissues, the overall effects were even less marked, with an average increase of MIP-1α by 1.4+0.2 fold (P=0.044), and of MIP-1β 1.5+0.1 (P=0.1).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting growth or replication of CCR5-tropic HIV-1 in human tissue, said method comprising contacting the tissue with an agent selected from the group consisting of: an attenuated human herpesvirus (HHV) and a killed or living human herpesvirus (HHV), wherein the HHV is HHV-6 or HHV-7.

2. A method of claim 1, in which the agent is an attenuated HHV-6.

3. A method of claim 2, wherein said HHV-6 is HHV-6A.

4. A method of claim 1, comprising administering to an individual infected with HIV-1 or exposed to HIV-1 an agent selected from the group consisting of: an attenuated human herpesvirus (HHV) and a killed or living human herpesvirus (HHV), wherein the HHV is HHV-6 or HHV-7.

* * * * *